(12) United States Patent
Schaller et al.

(10) Patent No.: US 10,194,988 B2
(45) Date of Patent: Feb. 5, 2019

(54) TORQUE LIMITING INSTRUMENT

(71) Applicant: DePuy Synthes Products, Inc., Raynham, MA (US)

(72) Inventors: Konrad Schaller, Grenchen (CH); Silas Zurschmiede, Grenchen (CH); Urs Hulliger, Deitingen (CH); Cyril Voisard, Niederbipp (CH)

(73) Assignee: DePuy Synthes Products, Inc., Raynham, MA (US)

( * ) Notice: Subject to any disclaimer, the term of this patent is extended or adjusted under 35 U.S.C. 154(b) by 468 days.

(21) Appl. No.: 14/598,597

(22) Filed: Jan. 16, 2015

(65) Prior Publication Data

US 2015/0202018 A1    Jul. 23, 2015

Related U.S. Application Data

(60) Provisional application No. 61/928,691, filed on Jan. 17, 2014, provisional application No. 61/928,713, filed on Jan. 17, 2014.

(51) Int. Cl.
*A61B 19/00* (2006.01)
*A61B 17/88* (2006.01)
(Continued)

(52) U.S. Cl.
CPC .......... *A61B 19/30* (2013.01); *A61B 17/8888* (2013.01); *A61B 90/03* (2016.02);
(Continued)

(58) Field of Classification Search
CPC ... A61B 19/30; A61B 90/03; A61B 2090/031; A61B 17/8888; B25B 23/14;
(Continued)

(56) References Cited

U.S. PATENT DOCUMENTS 176,811 A    5/1876  Richards
666,512 A    1/1901  Furbish
(Continued)

FOREIGN PATENT DOCUMENTS

CN    102019604       4/2011
CN    102019604 A     4/2011
(Continued)

OTHER PUBLICATIONS

U.S. Appl. No. 61/928,713, filed Jan. 17, 2014, Schaller et al.
(Continued)

*Primary Examiner* — Christopher M Koehler
*Assistant Examiner* — Henry Hong
(74) *Attorney, Agent, or Firm* — Baker & Hostetler LLP

(57) ABSTRACT

A torque limiting instrument is disclosed configured to drive a shaft to rotate in a select direction in response to an applied torque until the applied torque reaches a predetermined threshold. Thus, when the torque limiting instrument drives a bone screw into bone, the bone screw is advanced into the bone until the torque applied to the torque limiting instrument reaches the predetermined threshold, at which point the torque limiting instrument will no longer communicate the applied torque to the bone screw.

19 Claims, 10 Drawing Sheets

(51) Int. Cl.
*F16D 7/00* (2006.01)
*B25B 15/02* (2006.01)
*B25B 23/142* (2006.01)
*A61B 90/00* (2016.01)

(52) U.S. Cl.
CPC .......... *B25B 15/02* (2013.01); *B25B 23/1427* (2013.01); *F16D 7/002* (2013.01); *A61B 2090/031* (2016.02)

(58) Field of Classification Search
CPC ............ B25B 23/1427; B25B 23/1422; B25B 23/141; B25B 15/02
USPC .................. 81/467, 473, 474, 475, 59.1, 58
See application file for complete search history.

(56) References Cited

U.S. PATENT DOCUMENTS

| | | | |
|---|---|---|---|
| 2,439,980 A | 4/1948 | Livermont | |
| 3,157,258 A | 11/1964 | Cronholm | |
| 3,742,787 A | 7/1973 | Whiteford | |
| 4,249,435 A * | 2/1981 | Villeneuve | B25B 23/1427 81/477 |
| 4,262,501 A | 4/1981 | Vaughn et al. | |
| 4,687,392 A * | 8/1987 | Bidwell | F16B 31/02 411/432 |
| 5,002,555 A | 3/1991 | Petersen | |
| 5,507,211 A | 4/1996 | Wagner | |
| 5,615,587 A | 4/1997 | Foerster, Jr. | |
| 6,990,877 B1 * | 1/2006 | Wu | B25B 23/1427 81/467 |
| 7,181,997 B1 | 2/2007 | Rinner | |
| 7,484,440 B2 | 2/2009 | Wright | |
| 8,136,431 B2 * | 3/2012 | Wengreen | A61B 17/8875 81/467 |
| 8,172,003 B2 * | 5/2012 | Robieu | B24B 23/028 173/176 |
| 8,602,899 B2 | 12/2013 | You | |
| 2004/0159192 A1 | 8/2004 | Ping | |
| 2005/0072277 A1 * | 4/2005 | Knox | B25B 23/1427 81/467 |
| 2010/0055978 A1 * | 3/2010 | Montena | H01R 13/622 439/583 |
| 2010/0275744 A1 | 11/2010 | Wengreen et al. | |
| 2011/0162492 A1 | 7/2011 | Wilson et al. | |
| 2014/0083261 A1 * | 3/2014 | Wang | B25B 23/142 81/473 |
| 2015/0252855 A1 * | 9/2015 | Jakoubek | F16D 7/048 464/37 |

FOREIGN PATENT DOCUMENTS

| | | |
|---|---|---|
| DE | 3140288 A1 | 4/1983 |
| DE | 3149561 A1 | 6/1983 |
| DE | 3413761 A1 | 10/1985 |
| DE | 3808238 A1 | 10/1988 |
| DE | 4022763 A1 | 1/1991 |
| DE | 20314010 U1 | 1/2005 |
| DE | 102007051263 | 4/2009 |
| DE | 102011052442 B3 | 9/2012 |
| EP | 0019019 A1 | 11/1980 |
| EP | 1092510 B1 | 12/2009 |
| EP | 2023840 B1 | 1/2011 |
| GB | 319355 A | 8/1930 |
| GB | 599547 A | 3/1948 |
| TW | 410712 | 11/2000 |
| TW | 457172 | 10/2001 |
| TW | M306166 | 2/2007 |
| TW | M399002 | 3/2011 |
| TW | 201244888 A | 11/2012 |
| TW | 201330996 | 8/2013 |
| WO | WO 02/097386 | 12/2002 |
| WO | 2008/018865 | 2/2008 |
| WO | 2013/081934 A1 | 6/2013 |

OTHER PUBLICATIONS

U.S. Appl. No. 61/928,691, filed Jan. 17, 2014, Voisard et al.
U.S. Appl. No. 61/928,662, filed Jan. 17, 2014, Stank et al.
U.S. Appl. No. 14/598,530, filed Jan. 16, 2015, Stank et al.
TW Search report dated Jul. 25, 2018 for TW Application No. 104101411.

* cited by examiner

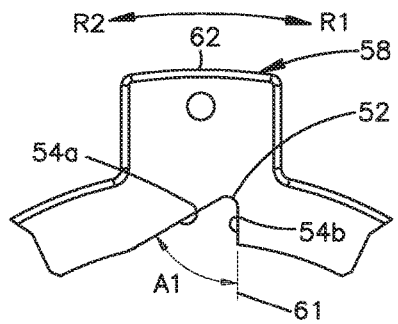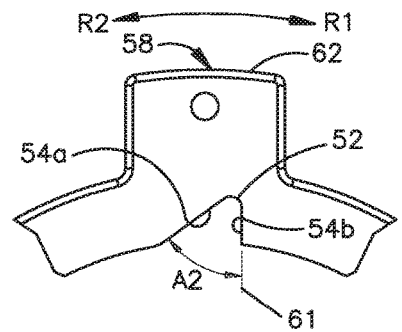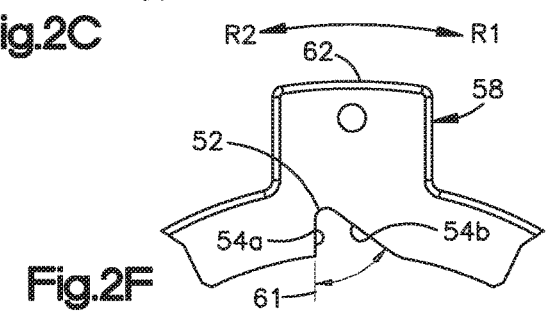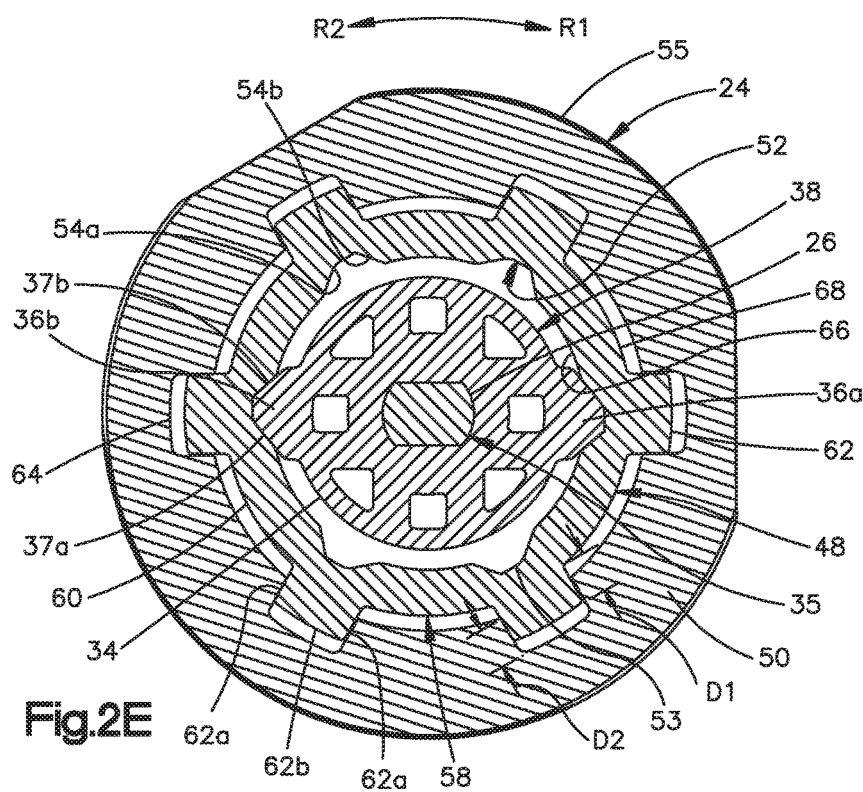

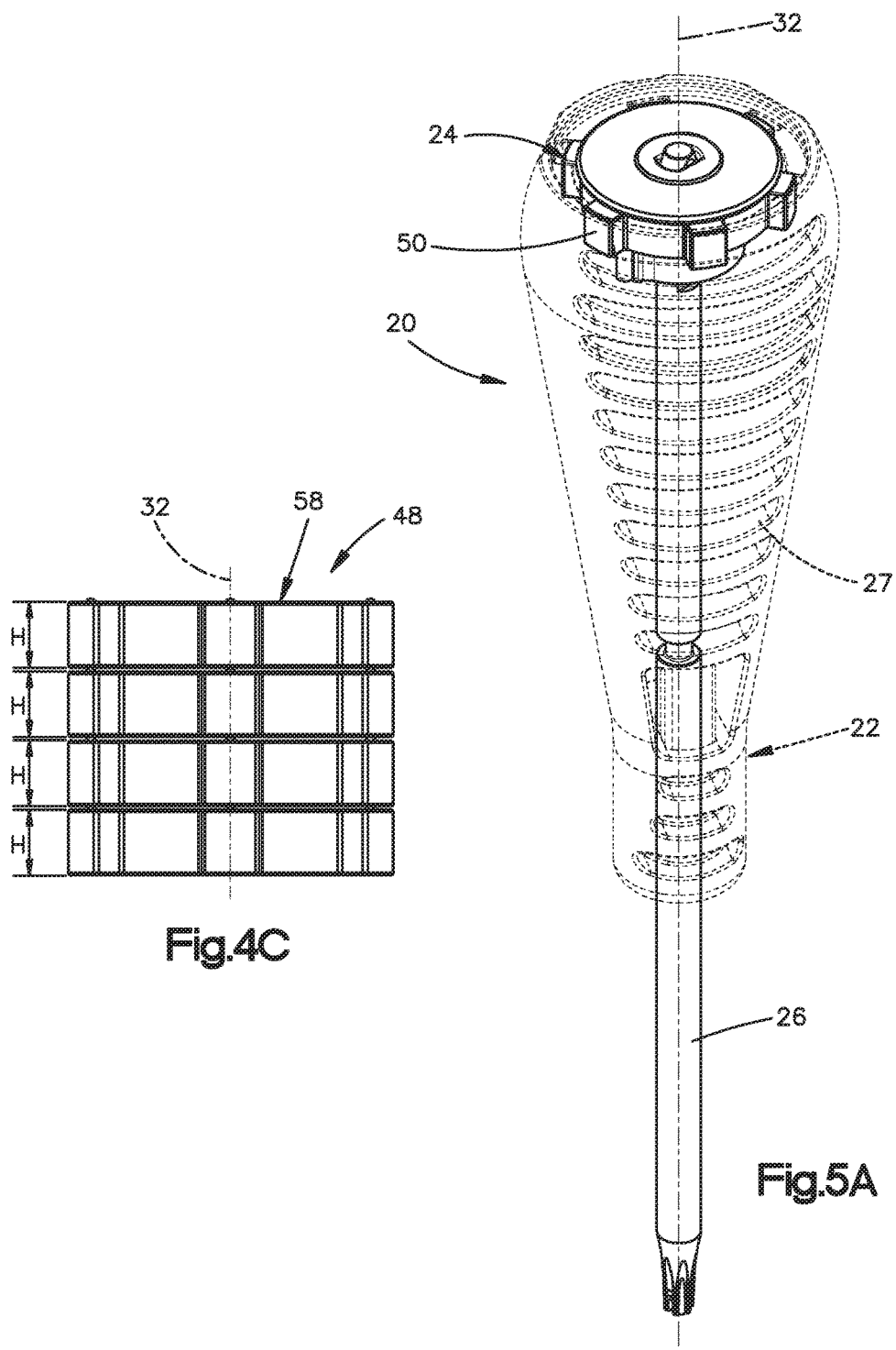

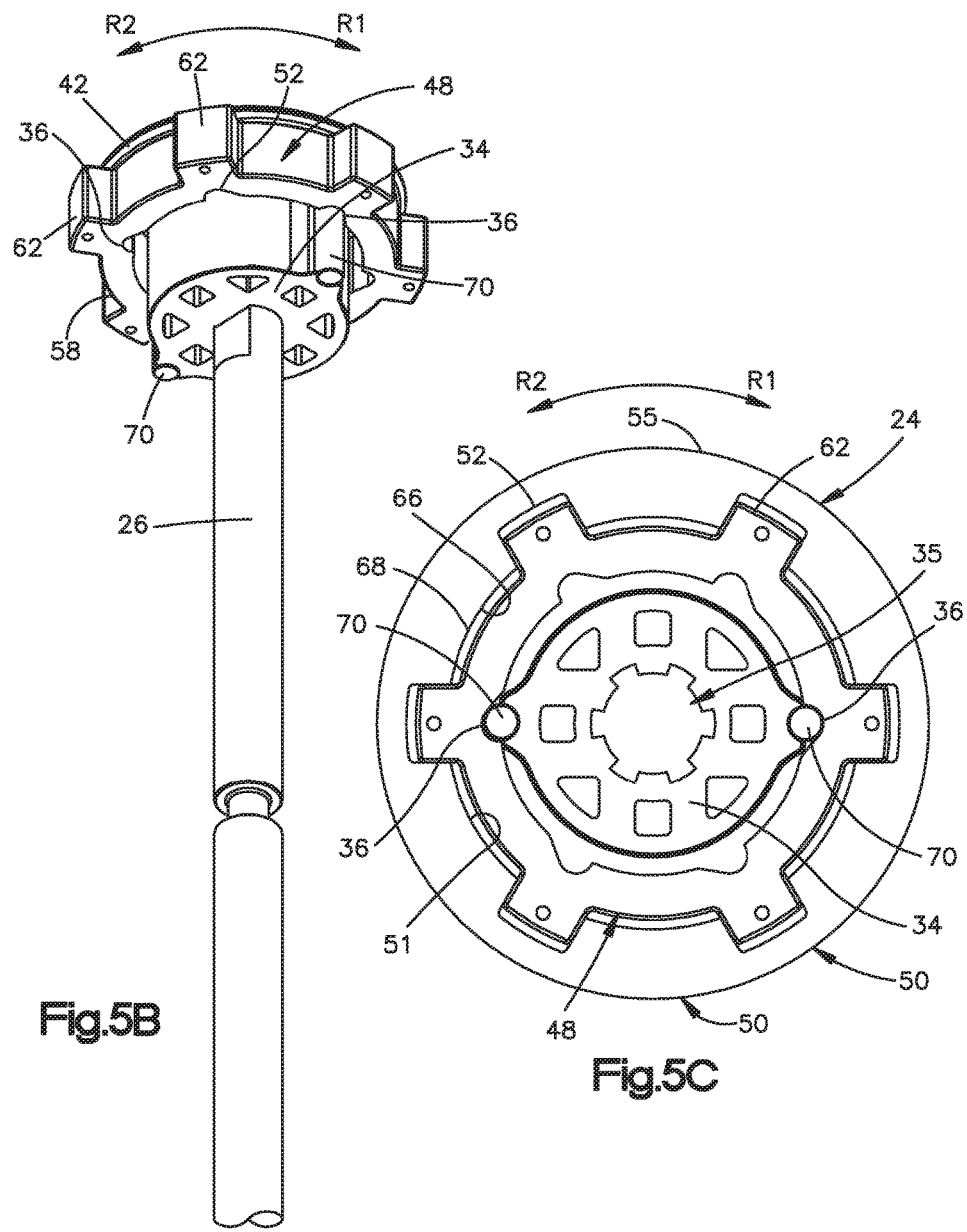

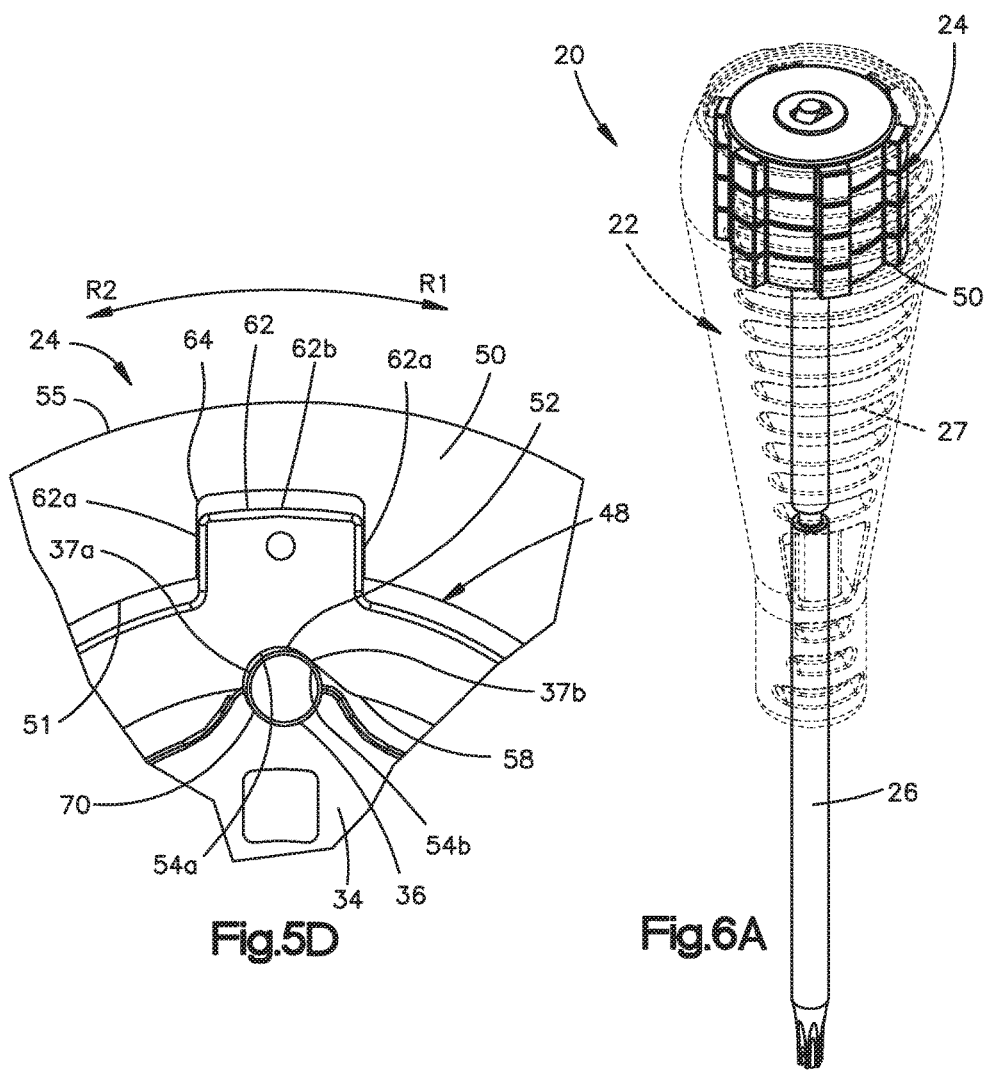

TORQUE LIMITING INSTRUMENT

CROSS-REFERENCE TO RELATED APPLICATIONS

This claims priority to U.S. Patent Application Ser. No. 61/928,691 filed Jan. 17, 2014, and further claims priority to U.S. Patent Application Ser. No. 61/928,713 filed Jan. 17, 2014, the disclosure of each of which is hereby incorporated by reference as if set forth in its entirety herein.

BACKGROUND

Surgical securement devices, such as surgical anchors, that fix implants to bone or other tissue are effective when used consistently with clinically tested protocols. In one example, surgical anchors configured as surgical screws are rotatably driven through an implant and into a target surgical location so as to fix the implant to the target surgical location. Surgical screws can be configured as bone screws that are driven through the implant, whereby the target surgical location is bone. Torque limiters are one type of device that surgeons can use to help position and appropriately lock the surgical anchor in place. Torque limiters can help ensure that no more than a desired torque is applied to the surgical anchor during implantation. Despite the use of torque limiters for medical applications, typical torque limiter designs are complex and costly to manufacture.

SUMMARY

In accordance with one embodiment, a torque limiting instrument includes a shaft that has a driving end, a cover, and an expansion member disposed between the shaft and the cover. The cover can be disposed radially outward with respect to the expansion member. The expansion member can be rotatably fixed to the cover, and can be configured to expand relative to the cover from a first position whereby the expansion member is rotatably coupled to the shaft to a second position whereby the expansion member is rotatably decoupled from the shaft such that the expansion member is rotatable about the shaft. The expansion member can be in the first position when a torque is applied to the cover in a first direction of rotation below a predetermined threshold, and an increase of the applied torque to the predetermined threshold can cause the expansion member to move from the first position to the second position.

BRIEF DESCRIPTION OF THE DRAWINGS

The foregoing summary, as well as the following detailed description of illustrative embodiments of the instrument of the present disclosure, will be better understood when read in conjunction with the appended drawings. It should be understood, however, that the application is not limited to the precise schematics and arrangements shown. In the drawings:

FIGS. 2C and 2D are schematic top plan views of a pocket of the torque transfer ring illustrated in FIG. 2A, shown in accordance with different embodiments;

FIG. 2E is a top plan view of the portion of the torque limiting instrument illustrated in FIG. 2A, but constructed in accordance with another embodiment;

FIG. 2F is a schematic top plan views of a pocket of the torque transfer ring illustrated in FIG. 2A, shown in accordance with another embodiment.

FIG. 4C is a side elevation view of the plurality of stacked torque transfer rings illustrated in FIG. 4A;

FIG. 5A is a perspective view of a torque limiting instrument constructed in accordance with an alternative embodiment;

FIG. 5B is a perspective view of a portion of the torque limiting instrument illustrated in FIG. 5A;

FIG. 5C is a sectional top plan view of a portion of the torque limiting instrument illustrated in FIG. 5A;

FIG. 5D is an enlarged sectional top plan view of a portion of the torque limiting instrument illustrated in FIG. 5A;

FIG. 6A is a perspective view of a torque limiting instrument similar to FIG. 5A, but including a plurality of stacked torque transfer rings in accordance with an alternative embodiment;

DETAILED DESCRIPTION

Figure 1:
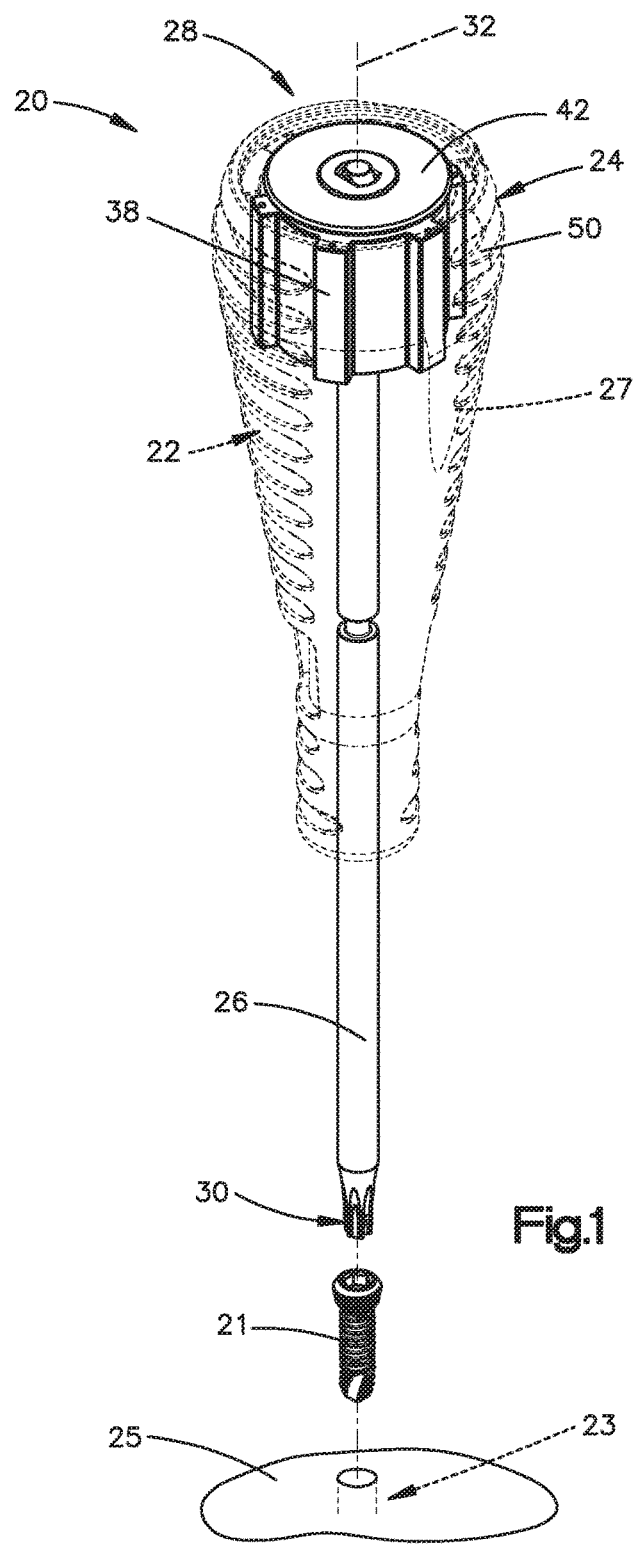
FIG. 1 is a cross-sectional perspective view of a torque limiting instrument constructed in accordance with one embodiment.

Referring to FIG. 1, a torque limiting instrument 20 comprises a driver that is configured to receive, be received by, or otherwise support or engage an anchor 21 and rotate the anchor so as to secure the anchor 21 to a target location 23. Thus, it should be appreciated that the anchor 21 can be configured as a screw. The target location 23 can be a target surgical location, and thus the anchor can be referred to as a surgical anchor. Thus, the instrument 20 can also be referred to as a torque limiting surgical screw driver in one configuration. In one application, the target surgical location is bone 25, and the surgical anchor can be referred to as a bone anchor. As will be described in more detail below, the instrument 20 is configured to apply no more than a predetermined torque to the anchor as the driver secures the anchor to the target location. Alternatively, the instrument 20 can be configured as a drill that is configured to create an opening in the target location 23.

The instrument 20 can include a handle 22, a torque transfer assembly 24 in communication with the handle 22, and a shaft 26 supported by the torque transfer assembly 24. The handle 22, the torque transfer assembly 24, and the shaft 26 can be made from a biocompatible plastic, metal, or any suitable alternative biocompatible material as desired unless otherwise indicated below. The handle 22 can define a grip member 27 that defines a proximal end 28 of the instrument 20. The instrument 20 can further define a distal end 30 that is spaced from the proximal end 28 along an axis 32 of the instrument 20. The axis 32 can extend along a longitudinal direction L or any other linear or nonlinear direction as desired. As used herein, the term "proximal" and derivatives thereof refer to a direction from the distal end 30 toward the proximal end 28. As used herein, the term "distal" and derivatives thereof refer to a direction from the proximal end 28 toward the distal end 30. The distal end 30 can be defined by the shaft 26 at a driving end of the shaft 26 that is configured to support the anchor so as to drive the anchor 21 into the target location 23 or otherwise support a drill bit or define a drill bit that is configured to create an opening in the target location.

The shaft 26 is elongate relative to the handle 22 along the axis 32 to the distal end 30. In accordance with one embodiment, the axis 32 can be defined by a central axis of the shaft 26. When a torque applied to the handle 22 in a first direction of rotation R1 is less than a predetermined threshold, an entirety of the applied torque is transferred through the torque transfer assembly 24 to the shaft 26 and thus to the anchor 21 that is supported by the shaft 26, such that the instrument 20 drives the anchor 21 into the target location 23. For instance, the torque can be applied to the grip member 27. The application of the torque can, for instance, be about the axis 32.

When the torque applied to the handle 22 in the first direction of rotation R1 is greater than the predetermined threshold, the force transfer assembly 24 causes the handle 22 to rotate relative to the shaft 26. Accordingly, the instrument 20 prevents torque greater than the predetermined threshold from being transferred to the shaft 26, and thus to the anchor 21 that is supported by the shaft 26. It will therefore be appreciated that the torque transfer assembly 24 prevents torque greater than the predetermined threshold from being transferred from the handle 22 to the shaft 26, and thus from the handle 22 to the anchor 21 that is supported by the shaft 26. The predetermined threshold can be defined by the torque transfer assembly 24 as described in more detail below.

Figure 2A:
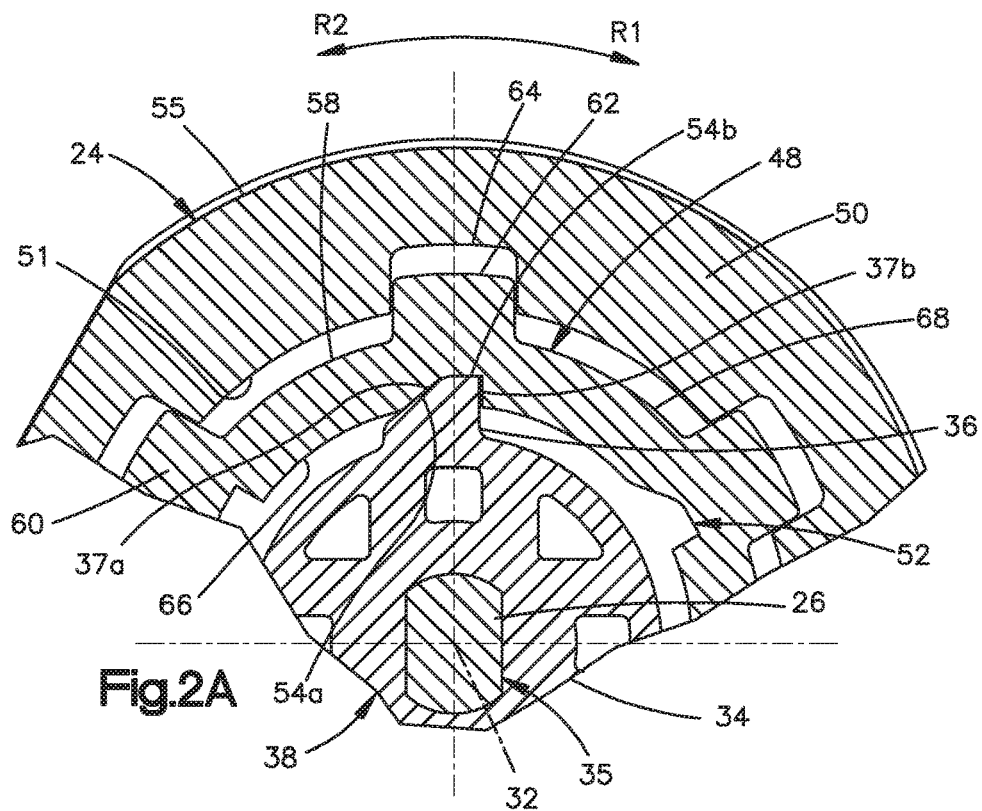
FIG. 2A is a sectional top plan view of a portion of the torque limiting instrument illustrated in FIG. 1, showing a cover, a torque transfer ring, a rocker, and a shaft.
Figure 2B:
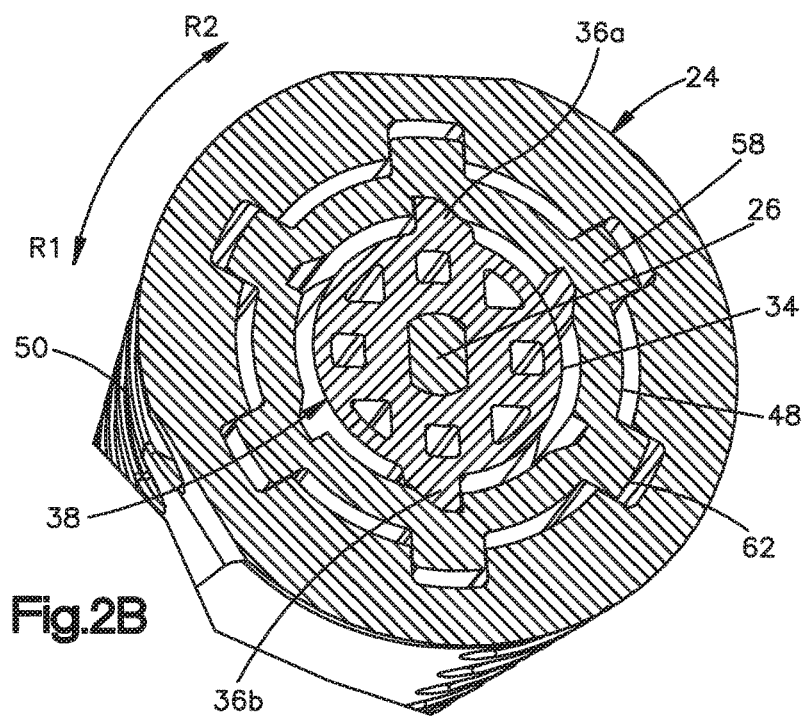
FIG. 2B is sectional bottom plan view of the torque limiting instrument illustrated in FIG. 2A, showing operation of the torque limiting instrument.

Referring now to FIGS. 1-2B, the torque transfer assembly 24 includes a cover 50 that is rotatably coupled to the grip member 27. Thus, a torque applied to the grip member 27 is similarly applied to the cover 50. For instance, the handle 22 can include the cover 50 that is monolithic with the grip member 27. Alternatively, the cover 50 can be rotatably coupled to the grip member 27 in any suitable embodiment as desired. For example, the cover 50 can be separate from and attached to the grip member 27. The torque transfer assembly 24 further includes a hub 34 that is rotatably fixed with respect to the shaft 26, and at least one biasing member 36 that extends radially outward with respect to the hub 34, and is rotatably fixed with respect to the hub 34. Thus, the at least one biasing member 36 rotates with the hub 34. For instance, the torque transfer assembly 24 can include a plurality of biasing members 36, such as first and second biasing members 36a and 36b, though it should be appreciated that the torque transfer assembly 24 can include as many biasing members 36 as desired. In accordance with one example, the biasing members 36 can be substantially equidistantly spaced circumferentially about the axis 32. Thus, the biasing members 36 can be substantially equidistantly spaced circumferentially about the hub 34. As illustrated, the first and second biasing members 36a and 36b are spaced substantially 180 degrees circumferentially from each other. The biasing members 36 can project out from an outer surface of the hub 34 any distance as desired, for instance a distance less than a radial distance from the axis 32 to the outer surface of the hub 34 from which the biasing members project. As illustrated in FIG. 2A, the hub can have a circular outer surface. As illustrated in FIG. 2B, the hub 34 can be elongate along a pair of elongate sides, and the hub 34 can define a pair of ends each connected between the elongate sides of the pair of elongate sides. The biasing members 36 can project out from respective ones of the ends. For instance, the first biasing member 36a can project out from a first one of the ends, and the second biasing member 36b can project out from a second one of the ends that is opposite the first one of the ends.

It should be appreciated that the term "radial" and derivatives thereof refer to a direction that is angularly offset, for instance perpendicular, with respect to the axis 32. For instance, the term "radially outward" and derivatives thereof can refer to a direction that is directed away from the axis 32, and can be aligned with the axis 32 or can be offset from the axis 32. The term "radially inward" and derivatives thereof can refer to a direction that is directed toward the axis 32, and can be aligned with the axis 32 or can be offset from the axis 32.

The biasing members 36 can be monolithic with the hub 34. For instance, the torque transfer assembly 24 can include a rocker member 38 that includes the hub 34 and the biasing members 36 that extend out from the hub 34. For instance, the hub and the biasing members can be co-planar with each other. Alternatively, the biasing members 36 can be separate from the hub 34 and rotatably coupled to the hub 34. For instance, the biasing members 36 can be separate from and attached to the hub 34, either directly or indirectly, so that the biasing members 36 rotate with the hub 34. As described above, the hub 34 is rotatably coupled with respect to the shaft 26. For instance, the hub 34 can be attached to the shaft 26. In accordance with the illustrated embodiment, the hub 34 defines an aperture 35 that receives the shaft 26. For example, the aperture 35 of the hub 34 and the shaft 26 can be noncircular in radial cross section, such that the hub 34 is rotatably coupled to the shaft 26. It should be appreciated, of course, that the hub 34 can be rotatably coupled to the shaft 26 in accordance with any suitable embodiment as desired. As will be described in more detail below, the biasing members 36 are configured to rotate about the axis 32, which causes the hub 34, and thus the shaft 26, to similarly rotate about the axis 32. The axis 32 can thus be a central axis of the aperture 35 of the rocker member 38.

Because the cover is rotatably fixed to the grip member 27, a torque applied to the grip member 27 about the axis 32 is transferred to the cover 50. When the shaft 26 has a load at the distal end 30 (for instance when the anchor 21 is supported by the distal end and engaging the target location 23, or when the distal end 30 is drilling into a target location), the torque can be applied to the cover 50 with respect to the shaft 26. The cover 50 extends, for example extends circumferentially, about the at least one biasing member 36, for instance about the plurality of biasing members 36, such that the biasing members 36 are disposed between the cover 50 and the hub 34. At least a portion of the cover 50 up to an entirety of the cover 50 can be disposed radially outward with respect to the biasing members 36. The cover 50 can support a plurality of pockets 52 that are configured to receive respective ones of the biasing members 36. As will be described in more detail below, when at least one of the pockets 52 receives a respective one of the biasing members 36, the cover 50 is rotatably coupled to the biasing members 36. Thus, when the cover 50 receives the applied torque, the cover 50 is driven to rotate about the axis 32 which causes the biasing members 36, and thus the hub 34, and thus the shaft 26, to similarly rotate about the axis 32. Furthermore, the biasing members 36 are configured to displace the pockets 52 radially outward with respect to the biasing members 36 until the biasing members 36 are removed from the pockets 52. When the biasing members 36 are removed from the pockets 52, the cover 50 is rotatably decoupled from the biasing members 36. Thus, when the cover 50 receives the applied torque, the cover 50 is driven to rotate about the axis 32 with respect to the biasing members 36, and thus the hub 34, and thus the shaft 26.

Referring now to FIGS. 1-3C, the torque transfer assembly 24 can further include an expansion member 48 that is disposed between the biasing members 36 and the cover 50. As will be described in more detail below, the expansion member 48 is rotatably fixed to the cover 50, and is configured to expand from a first position whereby the expansion member 48 is rotatably coupled to the biasing members 36 to a second position whereby the expansion member is rotatably decoupled from the biasing members 36, such that the expansion member is rotatable about the biasing members 36. The expansion member 48 is rotatably fixed to the cover 50. Furthermore, when the torque applied to the cover 50 in the first direction of rotation R1 is less than the predetermined threshold, the expansion member 48 is rotatably coupled with respect to the biasing members 36. Thus, when the torque applied to the cover 50 in the first direction of rotation R1 is less than the predetermined threshold, the expansion member 48 is rotatably coupled with respect to the shaft 26. When the torque applied to the cover 50 in the first direction of rotation R1 reaches the predetermined threshold, the expansion member 48 becomes rotatably decoupled with respect to the biasing members 36. Thus, when the torque applied to the cover 50 in the first direction of rotation R1 reaches the predetermined threshold, the expansion member 48 becomes rotatably decoupled with respect to the shaft 26. For instance, as described in more detail below, when the torque applied to the cover 50 in the first direction of rotation R1 reaches the predetermined threshold, the biasing members 36 urge the expansion member 48 radially outward with respect to the biasing members 36 to rotatably decouple the biasing members from the expansion member 48.

In one example, the expansion member 48 can be configured as a torque transfer ring 58 that extends circumferentially about the shaft 26. The torque transfer ring 58 can extend continuously about the shaft 26. For instance, the torque transfer ring 58 can have opposed terminal ends that are separate from each other and attached from each other. Alternatively, the terminal ends can be separate from and spaced from each other. The axis 32 can be a central axis of the torque transfer ring 58. The torque transfer ring 58 can define a torque transfer ring body 60 that is annular about the axis 32. The torque transfer ring 58 can further define at least one engagement tooth 62 such as a plurality of engagement teeth 62 project radially outward from the torque transfer ring body 60. For instance, the engagement teeth 62 can be co-planar with the torque transfer ring body 60. The teeth 62 can define respective side surfaces 62a that extend radially out from the outer surface 68 to a tip 62b that is connected between the side surfaces 62a. The side surfaces 62a can, for instance, be parallel to each other. Further, respective straight line extending perpendicular to the central axis 32 can bisect respective ones of the teeth 62. It should be appreciated, of course, that the teeth 62 can alternatively be sized and shaped as desired. Each of the engagement teeth 62 extend radially out from the torque transfer ring body 60 to an outer tip 62b. Each of the engagement teeth defines a distance from the torque transfer ring body 60 to the outer tip 62b a first distance D1. For instance, the outer tips 62b can be radially outer tips of the engagement tooth 62, and the first distance D1 can be measured along the radial direction.

The cover 50 can define a radially inner surface 51 and at least one recess 64, such as a plurality of recesses 64 that extends into the radially inner surface 51 along the radially outward direction. The recesses 64 are sized and dimensioned to receive a respective one of the engagement teeth 62 of the torque transfer ring 58 so as to rotatably couple the torque transfer ring 58 to the cover 50. The recesses 64 extend into the inner surface 51 a second distance D2 along the radial direction that can be substantially equal to, less than, or greater than the first distance D1 along the radial direction. For instance, the recesses 64 can terminate between the inner surface 51 and a radially outer surface 55 opposite the inner surface 51. Alternatively, the recesses 64 can extend from the inner surface 51 through the outer surface 55, in which case the second distance D2 is equal to the radial thickness of the cover 50.

Accordingly, during operation, the torque transfer ring 58 can be disposed in the first position whereby the engagement teeth 62 extend into respective ones of the recesses 64. Because the second distance D2 is greater than the first distance D1, the engagement teeth 62 are movable radially outward in the respective recesses 64 toward the outer surface 55, such that the torque transfer ring 58 is expandable radially outward with respect to the cover 50 from the first position to the radially expanded position. In one example, the torque transfer ring 58 can move from a circular shape in the first position to an oval shape in the expanded position. Thus, the torque transfer ring 58 can be flexible so as to move between the first position and the radially expanded position. The torque transfer ring 58 can have a stiffness that can be adjusted so as to correspondingly adjust the predetermined threshold as desired. For instance, increasing the stiffness of the torque transfer ring 58 can increase the predetermined threshold. The torque transfer ring 58 can be elastically flexible or plastically flexible as desired. It should be appreciated that the torque transfer ring 58 is rotatably fixed to the cover 50 both when the torque transfer ring 58 is in the first position and when the torque transfer ring 58 is in the expanded position.

During operation, a torque can be applied to the grip member 27, and thus to the cover 50. Application of the torque to the cover 50 in the first direction of rotation R1 causes the biasing members 36 to urge the torque transfer ring 58 radially outward so that the engagement teeth 62 move radially outward in the respective recesses 64. At the same time, the applied torque R1 in the first direction of rotation R1 causes the cover 50 to drive the biasing members 36 to rotate in the first direction of rotation R1 until the torque reaches a predetermined threshold. Because the hub 34 is rotatably coupled to the biasing members 36, and because the shaft 26 is rotatably coupled to the hub 34, rotation of the biasing members 36 in the first direction of rotation R1 drives the shaft 26 to rotate in the first direction of rotation R1. The first direction of rotation R1 can be a clockwise direction of rotation that is configured to drive the anchor 21 into the target location 23.

When the torque reaches the predetermined threshold, the biasing members 36 cause at least a portion of the torque transfer ring 58 to expand radially outward a sufficient distance such that the biasing members 36 become rotatably decoupled from the torque transfer ring 58. Thus, the cover 50 and torque transfer ring 58 rotate in the first direction R1 with respect to the biasing members 36 and the shaft 26 in response to the applied torque reaching the predetermined threshold. Thus, it can be said that the cover 50 is rotatably coupled to the biasing members 36 with respect to the first direction of rotation R1 until the torque applied to the cover 50 reaches the predetermined threshold, at which point expansion of the torque transfer ring 58 causes the cover 50 to become rotatably decoupled from the biasing members 36 in the first direction of rotation R1, so that the cover 50 is rotatable about the biasing members 36 in the first direction of rotation R1. Thus, rotation of the cover 50 in the first direction of rotation R1 does not cause the shaft 26 to rotate in the first direction of rotation R1. For instance, the torque transfer ring 58 can elastically expand radially outward in response to the biasing force of the biasing members 36, such that the torque transfer ring 58 can return toward the first position when the applied torque in the first direction of rotation R1 is reduced from the predetermined threshold, thereby again rotatably coupling the torque transfer ring 58 to the biasing members 36. Alternatively, the torque transfer ring 58 can plastically expand radially outward and does not return to the first position after removal of the applied torque in the first direction of rotation R1. In this regard, the instrument 20 can be referred to as a single use instrument.

The torque transfer ring body 60, and thus the torque transfer ring 58, defines a radially inner surface 66 and a radially outer surface 68 opposite the radially inner surface 66. The engagement teeth 62 project out from the radially outer surface 68. The torque transfer ring 58 can define at least one pocket 52 that extends radially outward into the inner surface 66 and terminates at an end 53. The at least one pocket 52 is sized and configured to receive the at least one biasing member 36. For instance, the torque transfer ring 58 can define a plurality of pockets 52 that are sized and configured to receive respective ones of the biasing members 36. The pockets 52 can be sized and configured to receive the biasing members 36. Because the torque transfer ring body 60 defines the pockets 52, and the torque transfer ring body 60 is supported by the cover 50, it should be appreciated that the cover 50 supports the pockets 52. Alternatively, the cover 50 can be expandable radially outward in response to the biasing force of the biasing members 36, and the cover 50 can define the pockets 52. As will now be described, the pockets 52 and the biasing members 36 are dimensioned such that the biasing members 36 bias the torque transfer ring 58 radially outward as a torque is applied to the cover 50 in the first direction of rotation R1. Accordingly, the pockets 52 receive the respective ones of the biasing members 36 when the applied torque is below the predetermined threshold, and eject the respective ones of the biasing members 36 when the applied torque reaches the predetermined threshold. One or more up to all of the pockets 52 can be aligned with a respective one of the engagement teeth 62. Further, one or more up to all of the engagement teeth 62 can be aligned with a respective one of the pockets 52.

For instance, with continuing reference to FIGS. 1-3C, each of the pockets 52 is at least partially defined by a respective first leading surface 54a and a first trailing surface 54b that is spaced from the first leading surface 54a along the first direction of rotation R1. Similarly, each of the biasing members 36 defines a second leading surface 37a and a second trailing surface 37b that is spaced from the second leading surface 37a along the direction of rotation R1. Each of the first and second leading surfaces 54a and 37a are inclined in the first direction of rotation R1 as they extend radially outward. Thus, the second leading and trailing surfaces 37a and 37b of each biasing member 36 can converge toward each other as they extend radially outward. Further, the first leading and trailing surfaces 54a and 54b of each pocket 52 can converge toward each other as they extend radially outward. It should be appreciated that each of the first and second leading surfaces 54a and 37a can be planar, curved or otherwise suitably shaped as desired. The first and second leading surfaces 54a and 37a can correspond with each other in shape, such that the first and second leading surfaces 54a and 37a are in surface contact with each other in the pocket 52, though the first and second leading surfaces 54a and 37a can define any suitable alternative contact characteristics as desired. Each of the first and second leading surfaces 54a and 37a can define any suitable angle A with respect to a straight radial line 61 that is perpendicular to the axis 32 and extends through the axis 32.

For instance, as illustrated in FIG. 2C, the torque transfer ring 58 can be constructed in accordance with one embodiment wherein the first leading surfaces 54a are inclined so as to define a first angle A1. As illustrated in FIG. 2D, the torque transfer ring 58 can be constructed in accordance with one embodiment wherein the first leading surfaces 54a are inclined so as to define a second angle A2 that is less than the first angle A1. As will be appreciated, the predetermined threshold can be determined in part by the angle A, such that the predetermined threshold increases as the angle A increases. As illustrated in FIGS. 7A-7E, the torque transfer ring 58 can include any number of pockets 52 as desired. The pockets 52 can be spaced circumferentially equidistantly from each other, or alternatively spaced from each other as desired. Further, the first leading and trailing surfaces 54a and 54b can define any suitable size and shape as desired. The torque transfer ring 58 can define include any number of pockets 52 as desired, for between two pockets and twenty-four pockets, depending on the frequency of instances of tactile feedback that is to be directed to the user during rotation of the cover 50 when the torque has reached the predetermined threshold.

During operation, when the torque is applied to the cover 50 in the first direction of rotation R1, the first leading surfaces 54a ride along the second leading surfaces 37a, such that the second leading surfaces 37a bias the torque transfer ring 58 to expand radially outward toward the cover 50. Thus, the engagement teeth 62 move into the respective pockets 52 as torque transfer ring 58 expands in response to an increase of the applied torque in the first direction of rotation R1. When the applied torque reaches the predetermined threshold, the torque transfer ring 58 expands radially outward a sufficient distance in response to the applied torque until the biasing members 36 travel out of the respective pockets 52. Otherwise stated, the second leading surfaces 37a engage respective ones of the plurality of first leading surfaces 54a, such that when the torque is below the predetermined threshold in the first direction of rotation R1, the first and second leading surfaces 54a and 37a engage such that the cover 50 drives the biasing members 36 to rotate in the first direction of rotation R1 only until the torque reaches the predetermined threshold, at which point the cover 50 and torque transfer ring 58 rotate in the first direction R1 relative to the plurality of biasing members 36. Thus, the first and second leading surfaces 54a and 37a are in abutment with each other when the applied torque in the first direction of rotation R1 is below the predetermined threshold, and are removed from abutment with each other when the applied torque in the first direction of rotation R1 reaches the predetermined threshold.

As the cover 50 and torque transfer ring 58 rotate about the biasing members 36, the inner surface of the torque transfer ring 58 rides along the biasing members 36. Further, the torque transfer ring 58 can move toward the first position when the biasing members 36 are aligned with sequentially adjacent pockets 52 as the torque transfer ring 58 rotates with respect to the biasing members 36. When the sequentially adjacent pockets 52 are aligned with respective ones of the biasing members 36, movement of the torque transfer ring 58 from the expanded position toward the first position can cause the aligned pockets 52 to receive the respective ones of the biasing members 36. Each instance that the biasing members 36 are received by sequentially adjacent pockets 52, contact between the biasing members 36 and the torque transfer ring 58 emits an audible "click" sound. Further, the user manually grasping the grip member 27 can feel differences in resistance of the handle 22 in response to the applied torque each instance that the biasing members 36 are received by the sequentially adjacent pockets 52. Accordingly, the instrument 20 can provide both tactile and acoustic feedback that the torque applied to the grip member 27 in the first direction of rotation R1 has reached the predetermined threshold. Because radially opposed first and second biasing members 36a-b move between sequentially adjacent pockets 52 that are radially opposite each other in response to the applied torque at the predetermined threshold, relative rotation between the torque transfer ring 58 and the biasing members 36 can produce substantially even strain and resulting wear on the torque transfer ring 58. It should be appreciated that the torque transfer ring 58 can define an interface between the first leading surface 54a and the inner surface 66. The interface can define a gradual transition between the first leading surface 54a and the inner surface 66, such that the biasing members 36 can transition smoothly from a position inside the respective ones of the pockets 52 to a position such that the inner surface 66 rides along the biasing members 36.

It should be appreciated that the torque transfer assembly 24 can include a first portion, which can include the cover 50 and the pockets 52 supported by the cover. In one example, the first portion can include the cover 50 and the torque transfer ring 58. The first portion is rotatably fixed with respect to the grip member 27. The torque transfer assembly 24 can further include a second portion that is rotatably fixed with respect to the shaft 26. The second portion of the torque transfer assembly 24 can include the hub 34 and the biasing members 36. The first and second portions are rotatably coupled to each other when the torque is applied to the grip member 27 that is below a predetermined threshold in a first direction of rotation R1. The torque transfer ring 58 can ride along the biasing members 36 so as to decouple the first portion of the torque transfer assembly 24 from the second portion of the torque transfer assembly 24 when the applied torque reaches the predetermined threshold in the first direction of rotation R1. For instance, as described above, expansion of the torque transfer ring 58 can cause the pockets 52 to eject the respective ones of the biasing members 36. Because the torque transfer assembly 24 rotatably decouples the grip member 27 from the shaft 26 when the applied torque in the first direction of rotation R1 reaches the predetermined threshold, the instrument 20 can drive a plurality of anchors 21 into respective target locations 23 with the same maximum amount of torque.

It is recognized that circumstances can make it desirable to remove an inserted anchor 21 from the respective target location 23. Thus, while the instrument 20 has been described as coupling the handle 22 to the shaft 26 only so long as the applied torque in the first direction of rotation is below the predetermined threshold, the handle 22 can be fixedly rotatable coupled to the shaft 26 with respect to a torque that is applied to the handle 22 in a second direction of rotation R2 that is opposite the first direction of rotation R1. Thus, the second direction of rotation R2 can be a counterclockwise direction.

For instance, at least one or both of the first and second trailing surfaces 54b and 37b can have at least a portion up to an entirety that is not inclined in the second direction of rotation R2 as it extends radially out with respect to the axis 32. Accordingly, the torque transfer ring 58, and thus the cover 50, is fixedly coupled to the biasing members 36 with respect to rotation in the second direction of rotation R2. For instance, at least a portion up to an entirety of at least one or both of the first and second trailing surfaces 54b and 37b can be perpendicular to the axis 32 and extend through the axis 32. Alternatively, at least a portion up to an entirety of at least one or both of the first and second trailing surfaces 54b and 37b can extend along the first direction of rotation R1 as they extend radially outward with respect to the axis 32. The at least a portion up to an entirety of at least one or both of the first and second trailing surfaces 54b and 37b can contact the other of the first and second trailing surfaces 54b and 37b in response to a torque applied to the cover 50 in the second direction of rotation R2. As described above, the torque applied to the grip member 27 in the second direction of rotation R2 is transferred to the cover 50.

During operation, when the torque is applied to the cover 50 in the second direction of rotation R2, the first trailing surfaces 54b apply a force to the respective second trailing surfaces 37b that urges the second trailing surfaces 37b, and thus the corresponding biasing members 36, to rotate in the second direction R2. Because the biasing members 36 are rotatably coupled to the hub 34, and the hub 34 is rotatably coupled to the shaft 26, rotation of the biasing members 36 in the second direction of rotation R2 causes the shaft 26 to rotate in the second direction of rotation R2. Further, as the cover 50 and the torque transfer ring 58 are biased by the applied torque to rotate in the second direction of rotation R2, the first trailing surface 54b does not ride along the second trailing surface 37b in the radially outward direction.

Alternatively, as illustrated in FIG. 2E, in accordance with one example, it is recognized that it may be desired to limit the torque applied to the shaft in the second direction of rotation R2. For instance, when removing an anchor from a target location, it may be desired to limit the amount of torque applied to the head of the anchor. Thus, in one example of the instrument 20, each of the first and second trailing surfaces 54b and 37b can be inclined in the second direction of rotation R2 as they extend radially out with respect to the axis 32. It should be appreciated that each of the first and second trailing surfaces 54b and 37b can be straight, curved or otherwise suitably shaped as desired. The first and second trailing surfaces 54b and 37b can correspond with each other in shape, such that the first and second trailing surfaces 54b and 37b are in surface contact with each other in the pocket 52, though the first and second trailing surfaces 54b and 37b can define any suitable alternative contact characteristics as desired. The first and second trailing surfaces 54b and 37b can define any suitable angle with respect to a straight radial line that is perpendicular to the axis 32 and extends through the axis 32.

Figure 4A:
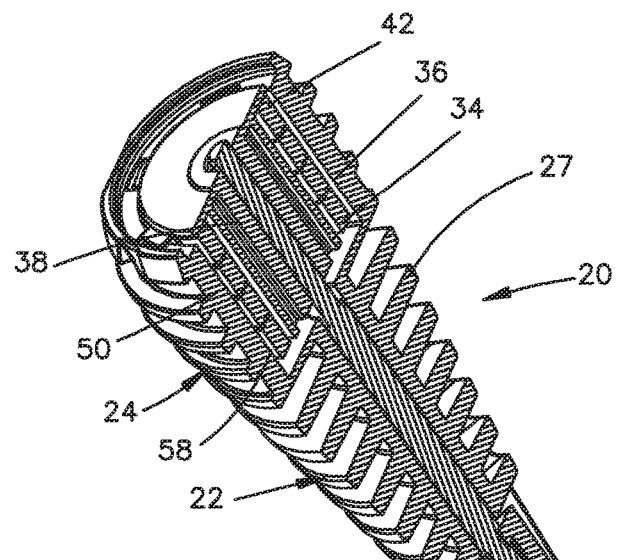
FIG. 4A is a perspective view of a torque limiting instrument similar to FIG. 1, but including a plurality of stacked torque transfer rings in accordance with an alternative embodiment.
Figure 4B:
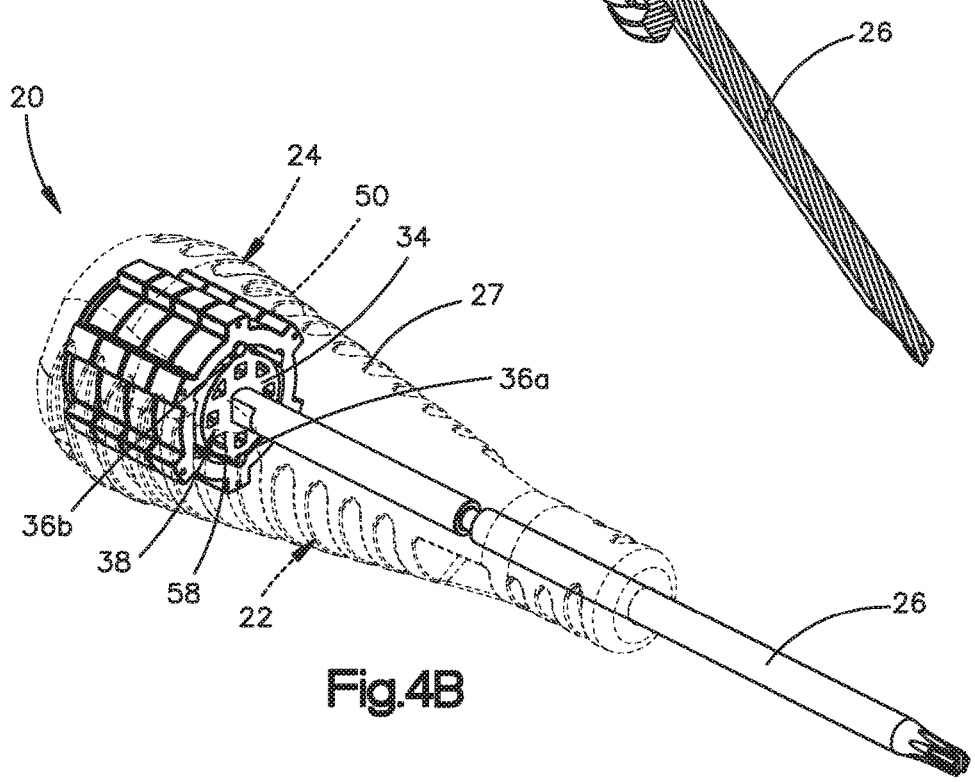
FIG. 4B is another perspective view of a portion of the torque limiting instrument illustrated in FIG. 4A.

Thus, during operation of the instrument as illustrated in FIG. 4B, when the torque is applied to the cover 50 in the second direction of rotation R2, the second trailing surfaces 37b bias the torque transfer ring 58 radially outward. For instance, as the cover 50 is driven to rotate in the second direction of rotation R2, the first trailing surfaces 54b ride along the second trailing surfaces 37b, which urges the torque transfer ring radially outward. When the applied torque in the second direction of rotation R2 reaches a second predetermined threshold, the biasing members 36 drive the torque transfer ring 58 to expand radially outward a sufficient amount so that the biasing members 36 travel out of the respective pockets 52. Otherwise stated, the second trailing surfaces 37b engage respective ones of the plurality of first trailing surfaces 54b, such that when the torque is below the second predetermined threshold in the second direction of rotation R2, the first and second trailing surfaces 54b and 37b engage so drive the biasing members 36 to rotate in the second direction of rotation R2 only until the torque reaches the predetermined threshold, at which point the cover 50 rotates in the second direction of rotation R2 relative to the plurality of biasing members 36. Thus, the first and second trailing surfaces 54b and 37b can be in abutment with each other when the applied torque in the second direction of rotation R2 is below the second predetermined threshold, and are removed from abutment with each other when the applied torque in the second direction of rotation R2 reaches the second predetermined threshold. The angle of the first and second trailing surfaces 54b and 37b can be equal to, greater than, or less than the angle of the first and second leading surfaces 54a and 37a. Accordingly, the second predetermined threshold can be equal to, greater than, or less than the predetermined threshold in the first direction of rotation R1.

As another example, referring to FIG. 2F, the first and second trailing surfaces 54b and 37b can be inclined as described above with respect to FIG. 2E. However, the first and second leading surfaces 54a and 37a can be constructed so as to have at least a portion that is not inclined in the first direction of rotation R1 as it extends radially outward. Accordingly, during operation, the torque limiting driving instrument limits the torque transferred from the cover 50 to the shaft 26 to the second predetermined threshold in the second direction of rotation R2, but does not limit the torque transferred from the cover 50 to the shaft 26 in the first direction of Rotation R1.

It is recognized that because the torque transfer ring 58 defines the first leading surface 54a and the first trailing surface 54b, and the torque transfer ring 58 is supported by the cover 50, that the cover 50 can be said to support the first leading surface 54a and the first trailing surface 54b. Furthermore, the first leading and trailing surfaces 54a and 54b and the complementary second leading and trailing surfaces 37a and 37b can be defined by any structure as desired. For instance, the first leading and trailing surfaces 54a and 54b can be defined by radially inward projections that extend radially in from the inner surface 66 of the torque transfer ring 58, which are thus supported by the cover 50, and the second leading and trailing surfaces 37a and 37b can be defined by pockets that extend into the radially outer surface of the hub 34.

A method of fabricating the instrument 20 can include the step of placing the torque transfer ring 58 about the shaft 26 such that the torque transfer ring 58 is rotatably coupled with respect to the shaft 26 the torque applied to the torque transfer ring 58 is below the predetermined threshold, and the torque transfer ring 58 is rotatably decoupled from the shaft 26 when the applied torque reaches the predetermined threshold. The torque can be in the first direction of rotation R1. Alternatively or additionally, the torque can be in the second direction of rotation R2. The method can further include the step of attaching the cover 50 to the torque transfer ring 58 so that the torque transfer ring 58 is rotatably fixed to the cover 50, such that the cover 50 is configured to receive the applied torque and transfer the applied torque to the torque transfer ring 58. The torque transfer ring 58 can expand toward the cover 50 when the applied torque reaches the predetermined threshold. The method can further include the step of fixing a plurality of biasing members 36 with respect to a shaft 26 so that the plurality of biasing members 36 are rotatably fixed to the shaft 26. For instance, the method can include the step of fixing the hub 34 to the shaft 26, and rotatably fixing the biasing members 36 to the hub 34. The method can further include the step of placing the torque transfer ring 58 between the cover 50 and the biasing members 36. For instance, the method can include the steps of placing the engagement teeth 62 into respective ones of the recesses 64. The method can further include the step of inserting the shaft 26 into the aperture 35 defined by the hub 34. The method can further include the step of inserting the biasing members 36 into respective ones of the pockets 52. The instrument 20, for instance the torque transfer assembly 24, can further include a seat 42 that can be fixed to the cover 50 and disposed distal with respect to the rocker member 38 and the torque transfer ring 58. Thus, the rocker member 38 and the torque transfer ring 58 can rest against the seat 42 so as to retain the rocker member 38 and the torque transfer ring 58 relative to each other and the cover 50 in the manner described above.

Figure 3A:
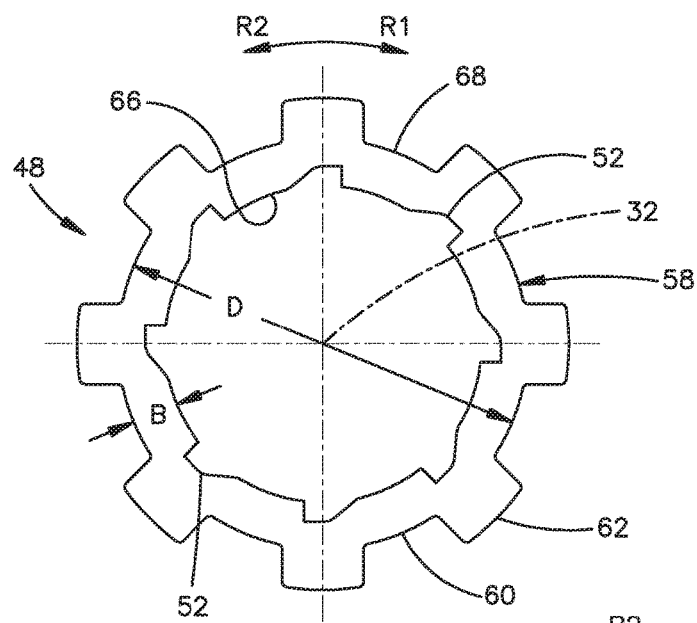
FIG. 3A is a top plan view of the torque transfer ring illustrated in FIG. 2A.
Figure 3B:
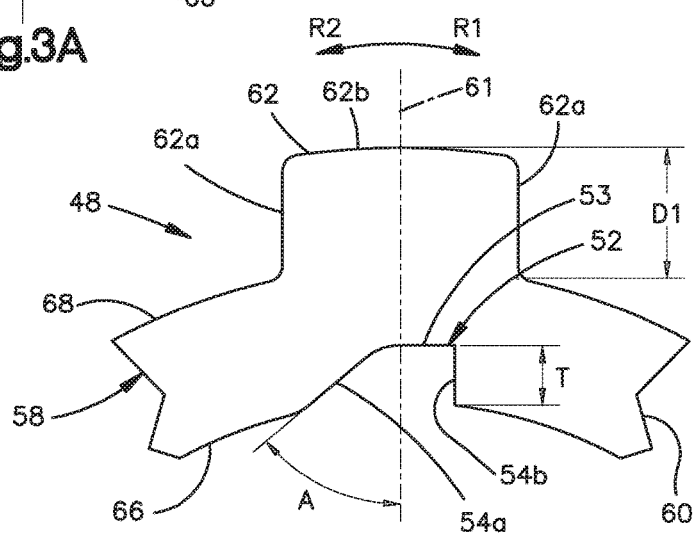
FIG. 3B is an enlarged top plan view of a portion of the torque transfer ring illustrated in FIG. 3A; showing a pocket of the torque transfer ring.
Figure 3C:
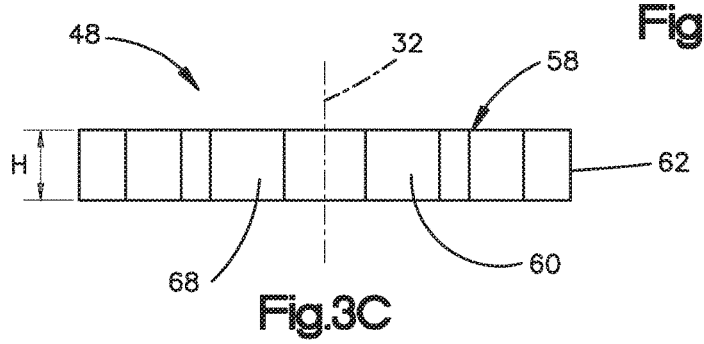
FIG. 3C is a side elevation view of the torque transfer ring illustrated in FIG. 3A.

Referring now to FIGS. 3A-3C in particular, the torque transfer ring 58 can at least partially define the predetermined threshold. For instance, the torque transfer ring 58 can define a depth B in the radial direction from the radially inner surface 66 to the radially outer surface 68. Further, the torque transfer ring 58 can define an outer cross-sectional dimension D as defined by the radially outer surface 68 along a straight radial line that is perpendicular to the axis 32 and intersects the axis 32. Further still, the pockets 52 can define the angle A as described above. Additionally, the torque transfer ring 58 can define a height H along a direction parallel to the axis 32. In this regard, it should be appreciated that the predetermined threshold can be at least partially determined by a number of factors, including one or more up to all of the depth B, the outer cross-sectional dimension D, the angle A, and the height H. Thus, a kit of instruments 20 can be provided, each having different predetermined thresholds. A bone fixation assembly can include one or more of the instruments 20 of the kit of instruments 20, one or more anchors 21, alone or in combination with one or more surgical implants.

Referring now to FIGS. 4A-4C, it should be appreciated that the instrument 20 can include as many torque transfer rings 58 as desired that are disposed adjacent each other along the shaft 26, and thus along the axis 32. Thus, the plurality of torque transfer rings 58 can define a corresponding plurality of rows of pockets 52 spaced from each other along the axis 32. The instrument 20 can further include a plurality of rockers 38 spaced from each other along the shaft 26, and thus along the axis 32. Thus, the plurality of rockers 38 can define a corresponding plurality of rows of biasing members 36 spaced from each other along the axis 32. One or more of the rockers 38 can be positioned radially offset with respect to one or more up to all of the other rockers 38, such that the respective first biasing members 36a are radially offset from each other, and the second biasing members 36b are radially offset from each other. It should be appreciated that the predetermined threshold can be increased by increasing the number of rows of rockers 38 and torque transfer rings 58. Alternatively or additionally, the rocker 38 can define an increased height so as to engage the respective rows of pockets 52 in the manner descried above.

The instrument 20 was tested with the following dimensions: D=37.5 mm, H=6 mm, T=0.8 mm, B=2.75 mm, and A=43 degrees. The material of the torque transfer ring 58 was Polyamide (PA) manufactured by Selective Laser Sintering (SLS). When the instrument 20 included one torque transfer ring 58, the predetermined threshold was found to be 0.45 Nm. When the instrument 20 included three torque transfer rings 58, the predetermined threshold was found to be 1.4 Nm. When the instrument 20 included six torque transfer rings 58 as illustrated in FIGS. 4A-4C, the predetermined threshold was found to be 2.75 Nm. When the instrument 20 with one torque transfer ring 58 was tested with the dimensions D=43 mm, H=6 mm, T=1.1 mm, B=4.0 mm, and A=47 degrees, the predetermined threshold was found to be 1.68 Nm. When the instrument 20 with four torque transfer rings 58 was tested with the dimensions D=43 mm, H=5.85 mm, T=1.6 mm, B=4.5 mm, and A=47 degrees, the predetermined threshold was found to be 10.7 Nm.

Referring now to FIGS. 5A-5D, and as described above, the torque transfer assembly 24 can include the hub 34 and the plurality of biasing members 36 that are rotatably coupled to the hub 34. The biasing members 36 can be monolithic with the hub as described above with respect to the rocker 38, or the biasing members 36 can be separate from the hub 34 as illustrated in FIGS. 5A-D. For example, the biasing members 36 can be configured as bearings 70 that are supported by the hub 34. The bearings 70 can be configured as ball bearings, roller bearings, or any suitable alternatively configured bearings as desired. The bearings 70 can be supported by the hub 34 in any manner as desired, and are configured to extend into the pockets 52 in the manner described above. For instance, the bearings 70 can be rotatably supported by the hub 34 so as to be rotatable with respect to the hub 34 about respective axes of rotation.

Thus, during operation, when the applied torque in the first direction R1 reaches the predetermined threshold, and the torque transfer ring 58 rides along the bearings 70, the bearings 70 in turn can roll along the respective ones of the leading surfaces 54a until the bearings 70 abut the inner surface 66 of the torque transfer ring 58. Continued application of the torque to the cover 50 in the first direction of rotation R1 causes the bearings 70 to roll along the inner surface 66 until the bearings 70 are inserted into sequentially adjacent pockets. Similarly, when the applied torque in the second direction R2 reaches the second predetermined threshold, and the torque transfer ring 58 rides along the bearings 70, the bearings 70 in turn can roll along the respective ones of the trailing surfaces 54b until the bearings 70 abut the inner surface 66 of the torque transfer ring 58. Continued application of the torque to the cover 50 in the second direction of rotation R2 causes the bearings 70 to roll along the inner surface 66 until the bearings 70 roll are inserted into an adjacent pockets.

Figure 6B:
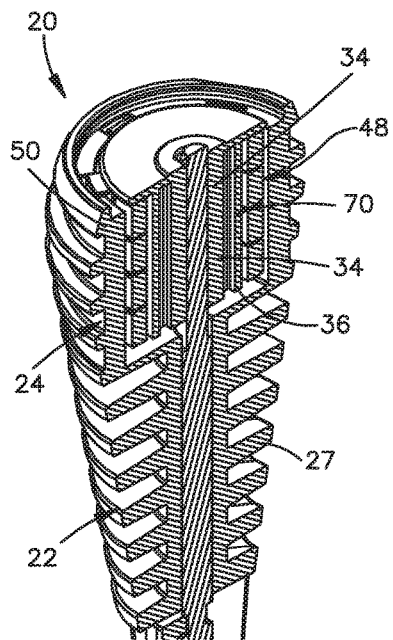
FIG. 6B is a cross-sectional perspective view of the torque limiting instrument illustrated in FIG. 6A.
Figure 7A:
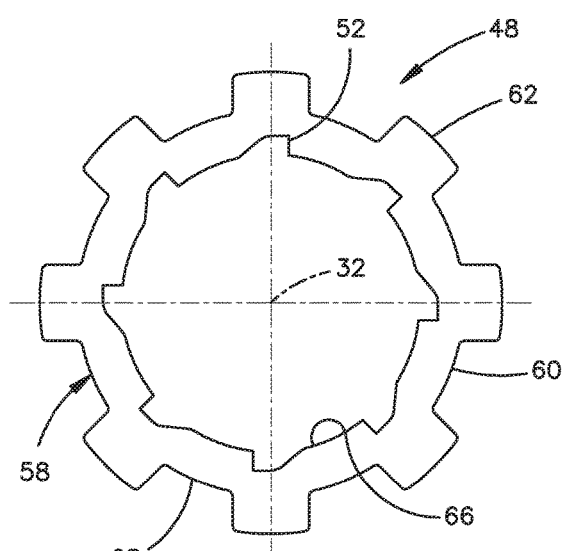
FIGS. 7A-7E are top plan views of the torque transfer ring constructed in accordance with various different embodiments.
Figure 7B:
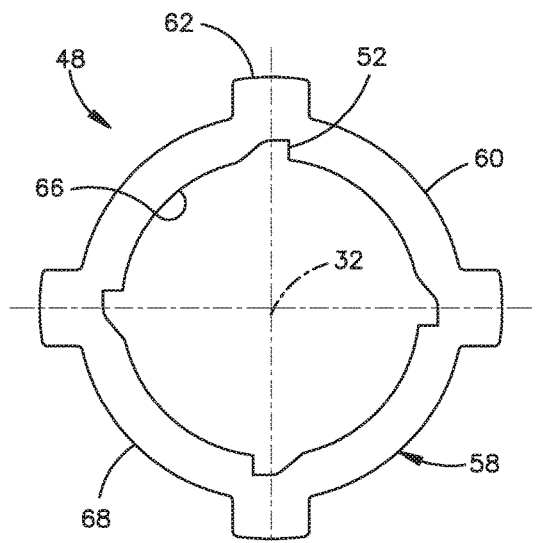
Figure 7C:
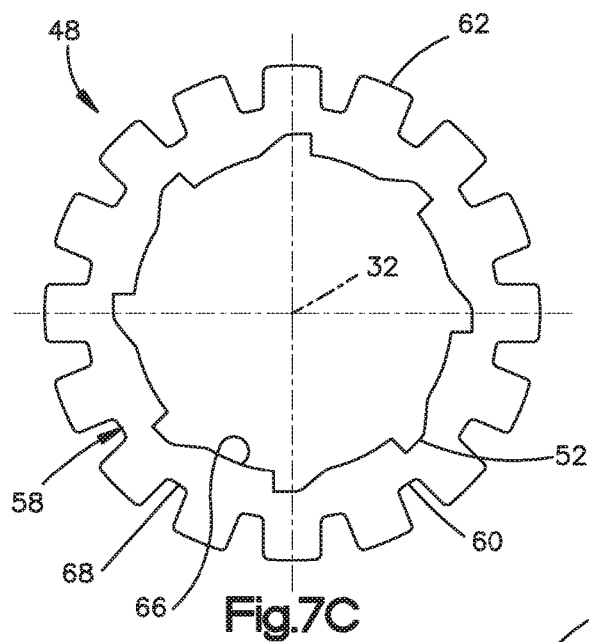
Figure 7D:
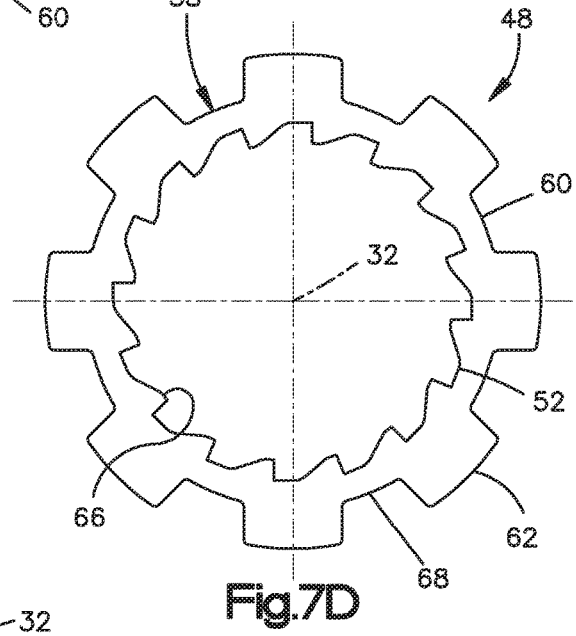
Figure 7E:
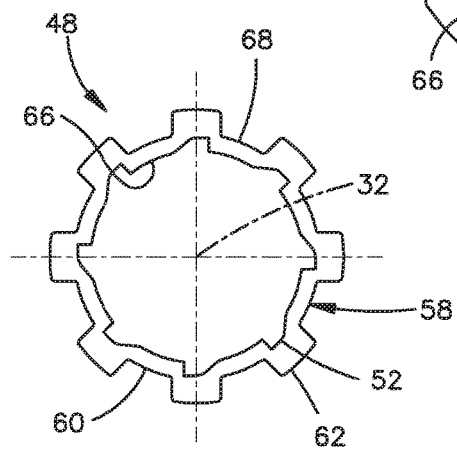

It should be appreciated that the bearings 70 can alternatively be rotatably supported by the torque transfer ring 58 and the pockets can be defined by the hub 34. Thus, during operation, when the applied torque in the first direction R1 reaches the predetermined threshold, the bearings 70 can roll along the hub 34 and out of the pockets so as to roll along the outer surface of the hub 34 to the adjacent pocket. Similarly, when the applied torque in the second direction R2 reaches the second predetermined threshold, the bearings 70 can roll along the hub 34 and out of the pockets so as to roll along the outer surface of the hub 34 to the adjacent pocket Referring now to FIGS. 6A-6B, and as described above with respect to FIGS. 4A-4C, it should be appreciated that the instrument 20 can include as many torque transfer rings 58 spaced along the shaft 26, and thus along the axis 32, as desired, and can further include as many rows of bearings 70 spaced along the shaft 26, and thus along the axis 32, as desired. The bearings 70 of one or more of the rows can be radially offset with respect to the bearings 70 of one or more others of the rows of bearings 70. The instrument 20 can include a corresponding plurality of torque transfer rings 58 that can define respective pockets 52 that are configured to receive the bearings 70 of the respective rows of bearings 70 in the manner described above. For example, the instrument 20 can include a plurality of hubs 34 each rotatably coupled with respect to the shaft 26 and spaced from each other along the axis 32, and each supporting a respective plurality of bearings 70. Alternatively or additionally, the hub 34 can define an increased height and can support a plurality of bearings 70 spaced along the axis 32 in respective rows so as to operably couple to the plurality of torque transfer rings 58 in the manner described above.

It is appreciated that a method can be provided for operating the instrument 20 as described above. For instance, the method can include the step of applying a torque to the cover 50 in the first direction of rotation R1 and, in response thereto, causing the cover 50 to correspondingly rotate the torque transfer ring 58 in the first direction of rotation R1, which urges the biasing members 36 to rotate in the first direction of rotation R1. The method can include the step of causing the biasing members 36 to apply a force to the torque transfer ring 58 that urges the torque transfer ring 58 to expand radially outward toward the cover. The method can include the step of applying the torque at the predetermined threshold and, in response thereto, causing the force applied by the biasing members 36 to cause the torque transfer ring 58 to expand radially outward toward the cover 50 a sufficient distance so that the cover 50 becomes rotatably decoupled from the biasing members 36. The method can then include the step of rotating the cover 50 relative to the biasing members 36 in the first direction of rotation R1.

The method can further include the steps of applying a second torque to the cover 50 in the second direction of rotation R2 opposite the first direction of rotation R1, and in response to the step of applying the second torque, causing the cover 50 to urge the biasing member 36 to rotate in the second direction of rotation R2. The method can further include the step of increasing the second applied torque to a second predetermined threshold, whereby the biasing members 36 bias the torque transfer ring 58 radially outward toward the cover 50 a sufficient distance so that the torque transfer ring 58 becomes rotatably decoupled from the biasing members 36. The step of increasing the second applied torque can cause the cover 50 to rotate relative to the biasing member 36 in the second direction of rotation R2.

It should be noted that the illustrations and discussions of the embodiments shown in the figures are for exemplary purposes only, and should not be construed limiting the disclosure. One skilled in the art will appreciate that the present disclosure contemplates various embodiments. Additionally, it should be understood that the concepts described above with the above-described embodiments may be employed alone or in combination with any of the other embodiments described above. It should further be appreciated that the various alternative embodiments described above with respect to one illustrated embodiment can apply to all embodiments as described herein, unless otherwise indicated.

What is claimed is:

1. A torque limiting instrument comprising:
a shaft having a driving end;
a cover that supports a first inclined leading surface, the cover spaced radially outward from the shaft, wherein the cover supports a plurality of pockets;
a rocker member that includes a biasing member, the biasing member disposed between the shaft and the cover, the biasing member defining a second inclined leading surface, wherein the biasing member is rotatably coupled to the shaft; and
an expansion member supported by the cover and disposed between the rocker member and the cover, the expansion member defining the plurality of pockets,
wherein when a torque that is applied to the cover in a first direction of rotation is less than a predetermined threshold, the biasing member extends into a respective one of the pockets, such that the first inclined leading surface abuts the second inclined leading surface so as to rotatably couple the biasing member to the cover with respect to the first direction of rotation, and when the applied torque increases to the predetermined threshold, the first inclined leading surface rides along the second inclined leading surface, which causes the biasing member to urge the expansion member to expand radially outward toward the cover, until the biasing member moves out of the respective one of the pockets whereby the first inclined leading surface no longer abuts the second inclined leading surface, thereby rotationally decoupling the cover from the biasing member, and
wherein the expansion member is rotatably coupled to the cover both before and after the applied torque reaches the predetermined threshold.

2. The torque limiting instrument as recited in claim 1, wherein each of the first inclined leading surface and the second inclined trailing surface is inclined in the first direction of rotation as it extends radially outward.

3. The torque limiting instrument as recited in claim 1, wherein the first inclined leading surface partially defines a respective one of the pockets and rides along the second inclined leading surface of the biasing member when the applied torque reaches the predetermined threshold, such that the biasing member is removed from the respective one of the pockets.

4. The torque limiting instrument as recited in claim 3, wherein the expansion member defines a plurality of engagement teeth that project radially outward, and the cover defines a plurality of recesses configured to receive respective ones of the engagement teeth so as to rotatably fix the expansion member to the cover, wherein the engagement teeth move radially outward within the recesses when the torque increases to the predetermined threshold.

5. The torque limiting instrument as recited in claim 1, wherein the rocker member comprises a hub that receives the shaft so as to rotatably couple the hub to the shaft, and the biasing member is rotatably fixed to the hub.

6. The torque limiting instrument as recited in claim 1, wherein the biasing member comprises a bearing that is configured to roll along the first inclined leading surface so as to urge the expansion member to expand toward the cover.

7. The torque limiting instrument as recited in claim 1, wherein the shaft extends axially out with respect to the cover.

8. The torque limiting instrument as recited in claim 1, wherein the driving end is configured to support a bone anchor and drive the bone anchor into bone.

9. The torque limiting instrument as recited in claim 1, wherein the driving end is configured to support or define a drill bit that is configured to create an opening in bone.

10. A torque limiting instrument comprising:
a shaft having a driving end;
a cover; and
an expansion member disposed between the shaft and the cover, such that the cover is disposed radially outward with respect to the expansion member, wherein the expansion member is rotatably fixed to the cover, and is configured to expand radially outward relative to the cover from a first position whereby the expansion member is rotatably coupled to the shaft to a second position whereby the expansion member is rotatably decoupled from the shaft such that the expansion member is rotatable about the shaft; and
a biasing member disposed between the shaft and the expansion member, the biasing member rotatably fixed to the shaft, wherein when the expansion member is in the first position, the expansion member is rotatably coupled to the biasing member, and when the expansion member is in the second position, the expansion member is rotatably decoupled from the biasing member such that the expansion member is rotatable about the biasing member,
wherein the expansion member is in the first position when a torque is applied to the cover in a first direction of rotation below a predetermined threshold, and an increase of the applied torque to the predetermined threshold causes the expansion member to move from the first position to the second position, and
wherein the applied torque causes the cover to rotate the expansion member in the first direction of rotation, such that the biasing member provides a force that urges the expansion member to expand radially outward.

11. The torque limiting instrument as recited in claim 10, wherein the expansion member defines a first inclined leading surface, the biasing member defines a second inclined leading surface configured to abut the first inclined leading surface when the applied torque is less than the predetermined threshold.

12. The torque limiting instrument as recited in claim 11, wherein the expansion member defines a plurality of first inclined leading surfaces, and a corresponding plurality of pockets partially defined by the plurality of first inclined leading surfaces, wherein the biasing member is disposed in a respective one of the plurality of pockets when the expansion member is in the first position.

13. The torque limiting instrument as recited in claim 12, wherein movement of the expansion member to the second position removes the biasing member from the respective one of the plurality of pockets.

14. The torque limiting instrument as recited in claim 12, wherein the expansion member defines a torque transfer ring that includes a flexible annular torque transfer ring body, and the pockets extend radially outward into the annular torque transfer ring body.

15. The torque limiting instrument as recited in claim 11, wherein the first inclined leading surface rides along the second inclined leading surface so as to move the expansion member from the first position to the second position when the applied torque in the first direction of rotation reaches the predetermined threshold.

16. The torque limiting instrument as recited in claim 11, wherein the biasing member comprises a bearing that is configured to roll along the first inclined leading surface so as to move the expansion member from the first position to the second position.

17. The torque limiting instrument as recited in claim 10, further comprising a hub that is rotatably fixed to the shaft and rotatably coupled to the biasing member.

18. The torque limiting instrument as recited in claim 10, wherein the expansion member is in the first position when a torque is applied to the cover below a second predetermined threshold in a second direction of rotation opposite the first direction of rotation, and an increase of the applied torque in the second direction of rotation to the second predetermined threshold causes the expansion member to move from the first position to the second position.

19. The torque limiting instrument as recited in claim 10, wherein the expansion member defines a plurality of engagement teeth that project radially outward, the cover defines a plurality of recesses configured to receive respective ones of the engagement teeth so as to rotatably fix the expansion member to the cover, and the engagement teeth move radially outward within the recesses as the expansion member moves from the first position to the second position.

* * * * *